US012620475B2

(12) United States Patent
Choi et al.

(10) Patent No.: US 12,620,475 B2
(45) Date of Patent: May 5, 2026

(54) INTERGRATED MEDICAL MANAGEMENT SYSTEM FOR INTERGRATING AND MANAGING DATA INCLUDING DATA LOCATED ON EXTERNAL SERVERS

(71) Applicant: IRM INC., Seoul (KR)

(72) Inventors: Seung Wook Choi, Seongnam-si (KR); Young Ryool Kwon, Ulsan (KR); Won Jun Hwang, Seoul (KR)

(73) Assignee: IRM INC., Seoul (KR)

( * ) Notice: Subject to any disclaimer, the term of this patent is extended or adjusted under 35 U.S.C. 154(b) by 403 days.

(21) Appl. No.: 18/143,551

(22) Filed: May 4, 2023

(65) Prior Publication Data

US 2023/0360775 A1 Nov. 9, 2023

(30) Foreign Application Priority Data

May 4, 2022 (KR) ........................ 10-2022-0055706

(51) Int. Cl.
*G06F 16/188* (2019.01)
*G16H 30/20* (2018.01)
(52) U.S. Cl.
CPC ........... *G16H 30/20* (2018.01); *G06F 16/188* (2019.01)
(58) Field of Classification Search
CPC .................................................... G06F 16/192
See application file for complete search history.

(56) References Cited

U.S. PATENT DOCUMENTS

| | | | | |
|---|---|---|---|---|
| 2002/0118815 A1* | 8/2002 | Andersen | ................ | H04M 3/60 |
| | | | | 379/265.09 |
| 2004/0165008 A1* | 8/2004 | Levine | .................... | G06F 9/451 |
| | | | | 715/789 |
| 2011/0202572 A1* | 8/2011 | Ho | ........................ | G16H 10/60 |
| | | | | 707/802 |

(Continued)

OTHER PUBLICATIONS

Luis Kuhn Cuellar et al., A data management infrastructure for the integration of imaging and omics data in life sciences, BMC Bioinformatics, Feb. 7, 2022, vol. 23, No. 61, pp. 1-20.

(Continued)

*Primary Examiner* — Bion A Shelden
(74) *Attorney, Agent, or Firm* — Studebaker Brackett PLLC

(57) ABSTRACT

The present disclosure relates to an integrated medical management system having at least: a medical data management device, a virtual folder management device, and a control device. The medical data management device receives, stores, and transmits medical data. The virtual folder management device creates a virtual folder in the virtual folder management device, and stores address information corresponding to a particular part of the medical data, in the virtual folder. The control device sets at least one condition for storing the medical data in the virtual folder, and controls the medical data management device and the virtual folder management device to selectively store the address information that meets the at least one condition, in the virtual folder. The virtual folder management device transmits, in response to an accessing request from the user device, the particular part of the stored medical data, corresponding to the address information, to the user device.

12 Claims, 9 Drawing Sheets

(56) References Cited

U.S. PATENT DOCUMENTS

| | | | |
|---|---|---|---|
| 2012/0005226 A1* | 1/2012 | Canessa | H04L 67/10 |
| | | | 707/769 |
| 2014/0278540 A1* | 9/2014 | Kyusojin | G16H 30/20 |
| | | | 705/3 |
| 2015/0098567 A1* | 4/2015 | Park | G06F 21/6272 |
| | | | 380/44 |
| 2019/0392187 A1* | 12/2019 | Hegendoerfer | G06K 7/10722 |
| 2020/0395119 A1* | 12/2020 | Lyman | G06Q 10/105 |
| 2021/0125705 A1* | 4/2021 | McGregor | G06F 16/9566 |
| 2021/0265041 A1* | 8/2021 | Narayanan | G16H 30/20 |

OTHER PUBLICATIONS

Fausto Milletari et al., Cloud Deployment of High-Resolution Medical Image Analysis With TOMAAT, IEEE Journal of Biomedical and Health Informatics, Dec. 5, 2018, vol. 23, No. 3, pp. 969-977.

* cited by examiner

Figure 4:
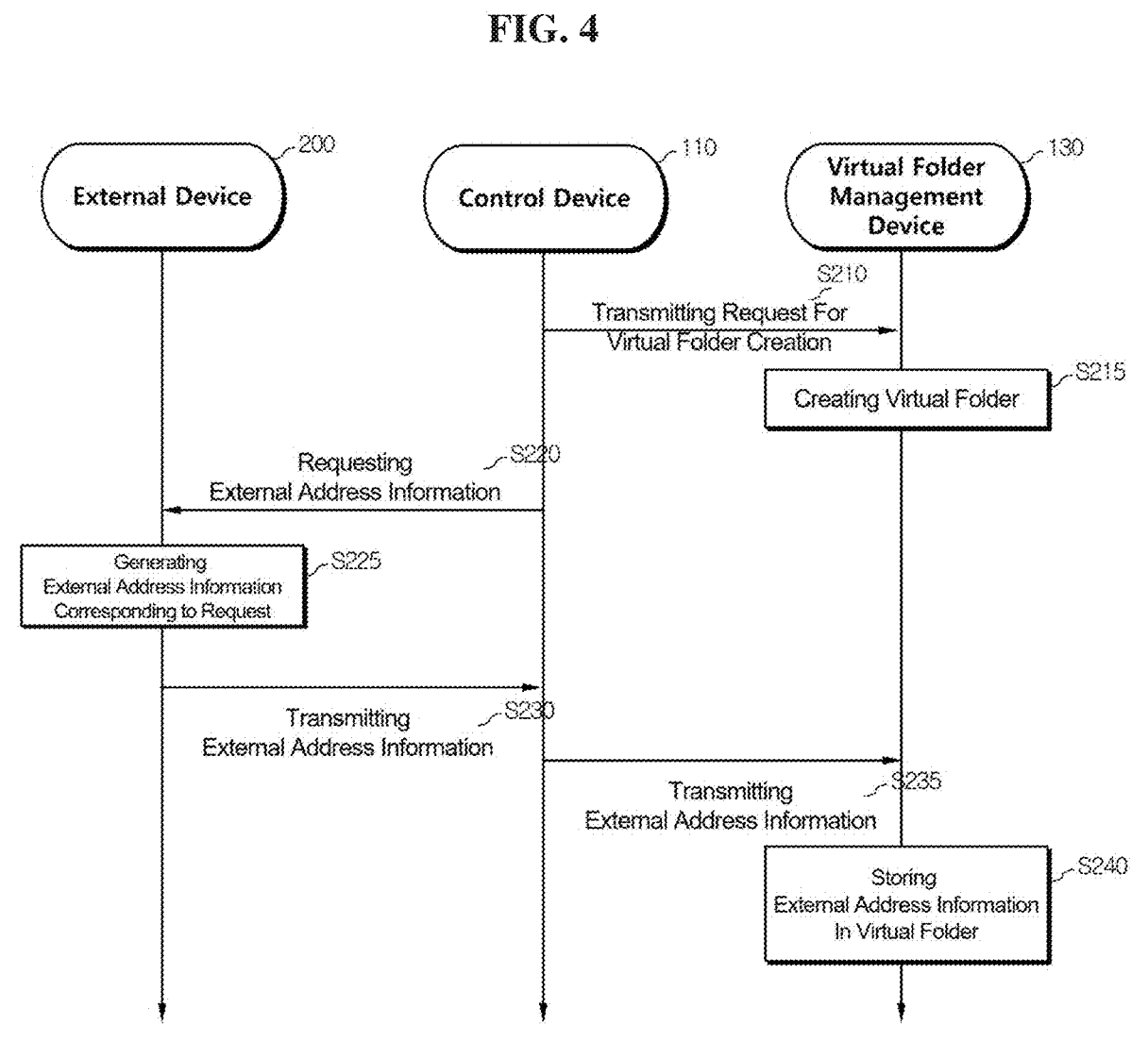

External Device — 200

Control Device — 110

Virtual Folder Management Device — 130

S210 — Transmitting Request For Virtual Folder Creation

S215 — Creating Virtual Folder

S220 — Requesting External Address Information

S225 — Generating External Address Information Corresponding to Request

S230 — Transmitting External Address Information

S235 — Transmitting External Address Information

S240 — Storing External Address Information In Virtual Folder

FIG. 6

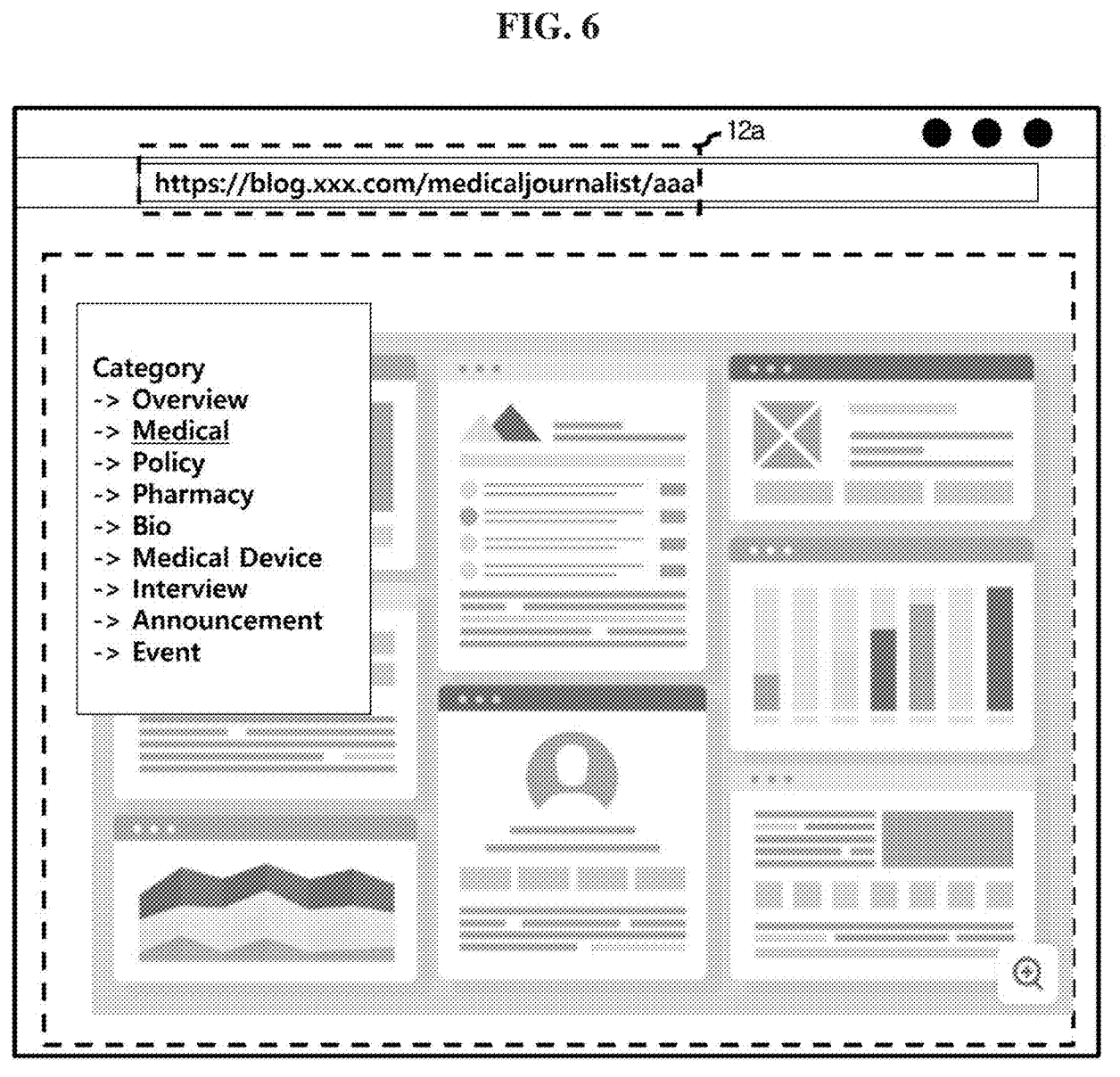

12a https://blog.xxx.com/medicaljournalist/aaa

Category
-> Overview
-> Medical
-> Policy
-> Pharmacy
-> Bio
-> Medical Device
-> Interview
-> Announcement
-> Event

FIG. 8

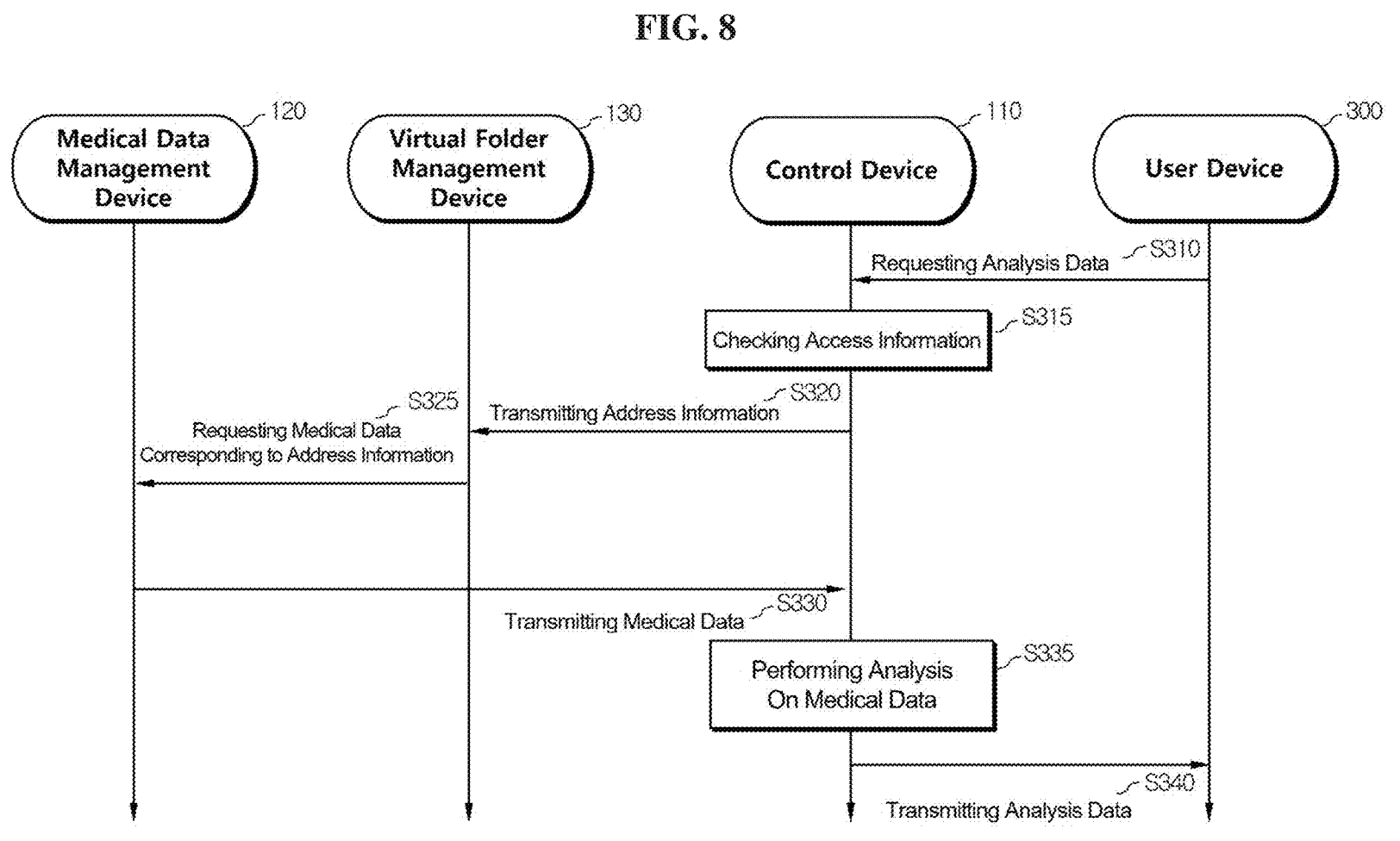

Medical Data Management Device — 120

Virtual Folder Management Device — 130

Control Device — 110

User Device — 300

S310 — Requesting Analysis Data

S315 — Checking Access Information

S320 — Transmitting Address Information

S325 — Requesting Medical Data Corresponding to Address Information

S330 — Transmitting Medical Data

S335 — Performing Analysis On Medical Data

S340 — Transmitting Analysis Data

INTERGRATED MEDICAL MANAGEMENT SYSTEM FOR INTERGRATING AND MANAGING DATA INCLUDING DATA LOCATED ON EXTERNAL SERVERS

CROSS-REFERENCE TO RELATED APPLICATIONS

The present application claims the benefit of priority to Korean Patent Application No. 10-2022-0055706, filed on May 4, 2022. The disclosures of the above-listed application are hereby incorporated by reference herein in its entirety.

TECHNICAL FIELD

The present disclosure generally relates to medical data management systems. More particularly, embodiments of the present disclosure generally relate to inventive and unconventional systems for receiving, integrating, storing and managing medical data including data located on an external device, and providing the medical data to a user device.

BACKGROUND

With the developments of computer and communication technology, the medical community is also researching and developing systems that provide medical services using computer and data communication technology. Numerous computerized medical image management systems exist. For example, Picture Arching Communication System (PACS), that is a medical imaging technology used primarily in healthcare organizations to securely store and digitally transmit electronic images and clinically-relevant reports, is introduced to eliminate the need to manually file and store, retrieve and send sensitive information, films and reports. With the PACS, the computer network is installed all over the hospital, all X-Ray films can be digitalized in database to be stored in a large central storage medium. A particular X-Ray film of the stored film data can be accessed by a computer monitor in an individual doctor's office.

These PACS can be configured as a centralized system or a distributed system, according to image data storage and request path methods.

The centralized system may store all image data in a large central storage medium and transmit the data to the requested system when requested. In the centralized system, all users (doctors) can access all image data regardless of time and place, but fast data transmission speed is required because data transmission can be made after an access request is received.

On the other hand, the distributed system distributes and stores image data in one or more storage media according to work characteristics. In the distributed system, each workstation has a cache-like local image storage characteristic that temporarily stores requested image data. The distributed system can be configured as a low-speed network that is relatively slow compared to the centralized system, but there is a disadvantage that data transmission takes some time when requested image data is not stored in a local workstation.

Meanwhile, with the recent increase in demand for remote medical data processing, various data processing companies are providing software for medical data processing. The demand for platforms that may process multiple types of medical software is also increasing.

2

SUMMARY

One aspect of the present disclosure is directed to a system for receiving, integrating, storing and managing medical data, and providing the medical data to a user device. The system may include: a medical data management device comprising a hardware processor and a hardware memory; a virtual folder management device comprising a hardware processor and a hardware memory; and a control device comprising a hardware processor and a hardware memory. The hardware processor of the medical data management device may receive medical data through an input interface of the medical data management device, store the received medical data in the hardware memory of the medical data management device, and transmit the stored medical data to at least one selected from the group consisting of the virtual folder management device, the control device, and one or more external devices. The hardware processor of the virtual folder management device may create a virtual folder in the virtual folder management device, and store, in response to a request for storing, received from a user device, address information corresponding to a particular part of the stored medical data, in the virtual folder. The hardware processor of the control device may set at least one condition for storing the medical data in the virtual folder, and control the medical data management device and the virtual folder management device to selectively store the address information that meets the at least one condition, in the virtual folder. The hardware processor of the virtual folder management device may transmit, in response to a request for accessing, received from the user device, the particular part of the stored medical data, corresponding to the address information, to the user device.

Other features of the inventive concept are included in the detailed description and drawings.

TECHNICAL IMPROVEMENT

The integrated medical data management systems according to some embodiments of the present disclosure may provide a large amount of medical data to a user by storing an address that can access data located on an external device as well as an internal medical data management device.

According to the conventional arts, the process of accessing data stored in an external server was a way for users to access the desired data by entering layered folders one by one. This way would take multiple steps of operations. By contrast, the present disclosure provides a way to efficiently access data stored in other servers by obtaining address information on medical data stored in other servers. In this way, multiple operations for entering folders one by one are unnecessary.

Furthermore, by utilizing address information as described in the present disclosure, it is possible to reduce the number of data transfers required for data analysis. According to the conventional arts, when pre-analysis medical data are existed on an external server, medical data should be received by a processing device from the external server, and once the data was analyzed, the analyzed data had to be transmitted back on the external server. By contrast, the present disclosure providing a way to receive analyzed medical data by performing analysis on an external server through dynamic address information without directly receiving medical data before analysis, thereby reducing the number of data transmissions. In this way, network resources can be saved, and also, the risk of data leakage can be reduced.

Furthermore, the integrated medical data management systems according to some embodiments of the present disclosure may provide medical data subscription services by creating a virtual folder corresponding to one or more conditions set by the user and providing a user with an address indicating the stored medical data.

Furthermore, the integrated medical data management systems according to some embodiments of the present disclosure may load function data stored on an external device according to a user input that requests data processing for medical data, and may provide user-customized data processing results using less storage space.

The technical improvements obtained from the exemplary embodiments of the present disclosure are not limited to the above-mentioned technical improvements, and other technical improvements not mentioned may be derived and understood by a person ordinary skilled in the art to which the exemplary embodiment of the present disclosure relates. That is, technical improvements of implementing the exemplary embodiments of the present disclosure may also be derived from the exemplary embodiments of the present disclosure by a person ordinary skilled in the art.

BRIEF DESCRIPTION OF THE FIGURES

The above and other objects and features will become apparent from the following description with reference to the following figures, wherein like reference numerals refer to like parts throughout the various figures unless otherwise specified, and wherein:

FIG. 1 is a diagrammatic illustration of an exemplary integrated medical data management system according to some embodiments of the present disclosure.

FIG. 3 is a flow chart illustrating an exemplary process of storing address information corresponding to medical data in a virtual folder, according to some embodiments of the present disclosure.

FIG. 4 is a flow chart illustrating an exemplary process of storing external address information from an external device in a virtual folder according to some embodiments of the present disclosure.

FIG. 6 is exemplary medical data provided to a user based on static address information according to some embodiments of the present disclosure.

FIG. 8 is a flow chart illustrating an exemplary process of providing result data for medical data after confirming user access information, according to some embodiments of the present disclosure.

FIG. 9 is another diagrammatic illustration of an exemplary integrated medical data management system according to some embodiments of the present disclosure.

DETAILED DESCRIPTION

Figure 2:
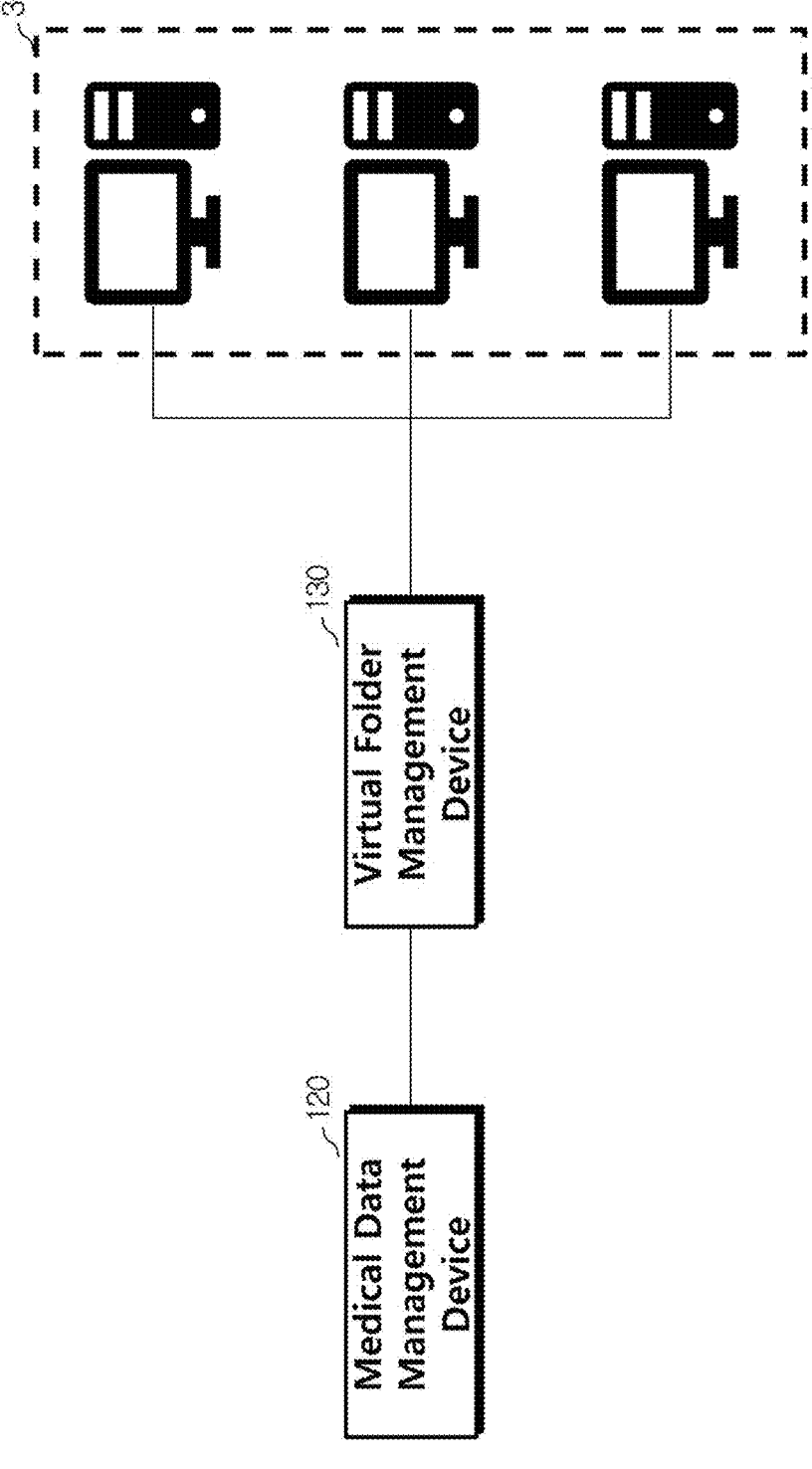
FIG. 2 is a diagrammatic illustration of an exemplary system for providing medical data to a user according to some embodiments of the present disclosure.

Advantages and features of the inventive concept, and methods of achieving them will become apparent with reference to embodiments described below in detail in conjunction with the accompanying drawings. However, the inventive concept is not limited to the embodiments disclosed below, but may be implemented in various forms. The present embodiments are provided to merely complete the disclosure of the inventive concept, and to inform merely fully those skilled in the art of the inventive concept of the scope of the inventive concept. The inventive concept is only defined by the scope of the claims.

The terminology used herein is for the purpose of describing the embodiments only and is not intended to limit the inventive concept. As used herein, the singular forms "a" and "an" are intended to include the plural forms as well, unless the context clearly indicates otherwise. It will be further understood that the terms "comprises", "comprising", "includes", and "including" when used in this specification, specify the presence of the stated features, integers, operations, elements, and/or components, but do not preclude the presence or addition of one or more other features, integers, operations, elements, components, and/or portions thereof. Like reference numerals refer to like elements throughout the disclosure. As used herein, the term "and/or" includes any and all combinations of one or more of the associated listed items. Although terms "first", "second", etc. are used to describe various components, it goes without saying that the components are not limited by these terms. These terms are only used to distinguish one component from another component. Therefore, it goes without saying that a first component as mentioned below may be a second component within a technical idea of the inventive concept.

Unless otherwise defined, all terms including technical and scientific terms used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Spatially relative terms "below", "beneath", "lower", "above", "upper", and the like may be used to easily illustrate a correlation between components as shown in the drawings. The spatially relative terms should be understood as terms including an orientation of a component varying in use or operation in addition to an orientation as shown in the drawings. For example, when a drawing is turned over, a first component described as "below" or "beneath" a second component may be placed "above" the second component. Accordingly, the exemplary term "below" may include both "below" and "above". A component may be oriented in a varying direction. Accordingly, the spatially relative terms may be interpreted according to the orientation.

Hereinafter, an embodiment of the present invention will be described in detail with reference to the accompanying drawings.

Figure 1:
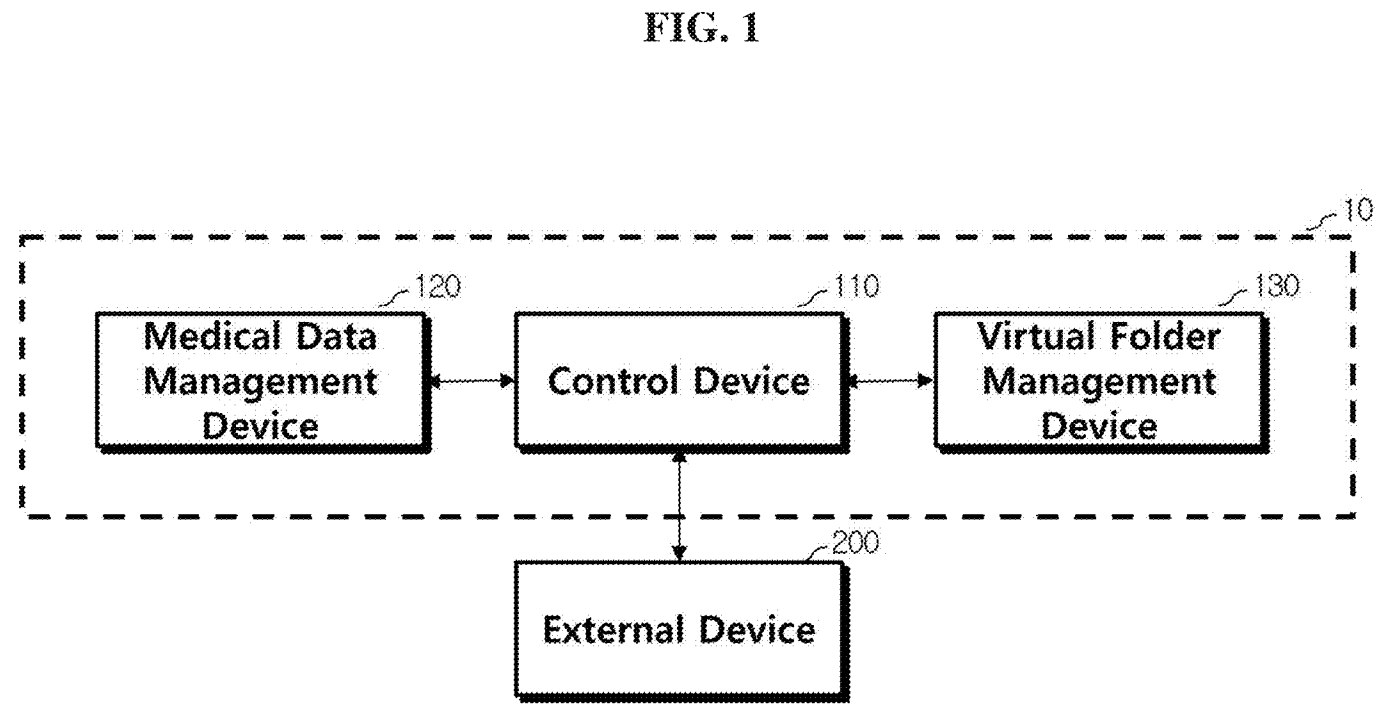

FIG. 1 is a diagrammatic illustration of an exemplary integrated medical data management system according to some embodiments of the present disclosure.

Referring to FIG. 1, the integrated medical data management system 10 according to some embodiments of the present disclosure may include a control device 110, a medical data management device 120, and a virtual folder management device 130.

Herein, in some embodiments, the control device 110, the medical data management device 120, and the virtual folder management device 130 may be connected with wireless communication or wired communication. In such connection, at least one selected from wireless Internet such as Wi-Fi wireless fidelity, portable Internet such as 802.11x (e.g., 802.11a, 802.11b, 802.11g, 802.11n, 802.11ac), WiBro (wireless broadband internet) or WiMAX (world interoperability for microwave access), a 2G (Second Generation) mobile communication network, such as GSM (global system for mobile communication) or CDMA (code division multiple access), a 3G (Third Generation) mobile communication network, such as WCDMA (wideband code division multiple access) or CDMA2000, a 3.5G mobile communication network, such as HSDPA (high speed downlink packet access) or HSUPA (high speed uplink packet access), a 4G (Fourth Generation) mobile communication network, such as LTE (long term evolution network) or LTE-Advanced (LTE-A) network, 5G (Fifth Generation) mobile communication network, UWB (Ultra-Wide Band), Bluetooth, Zigbee, a satellite communication network, and combinations thereof, can be used.

Figure 9:
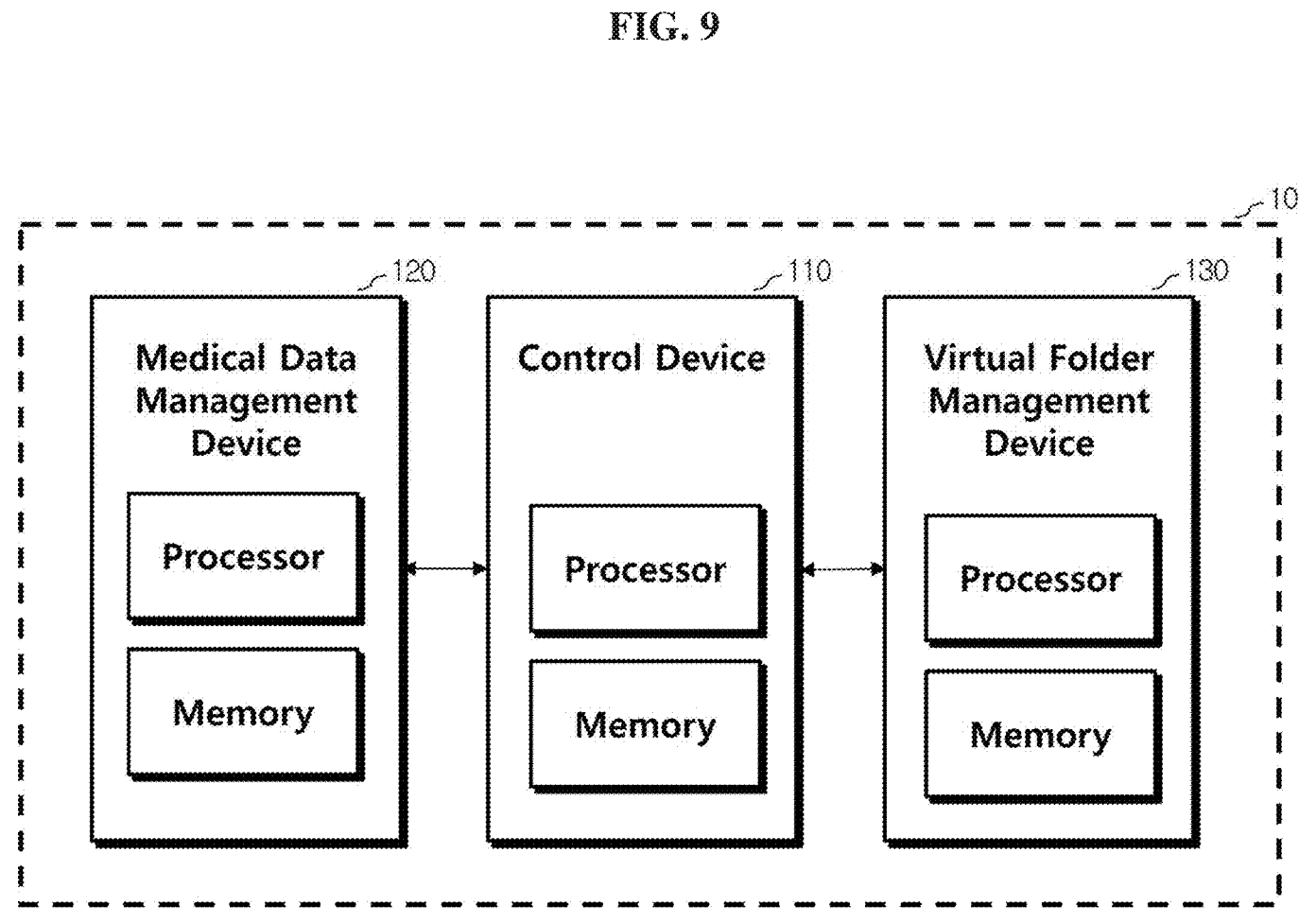

In some embodiments, the control device 110 may include a hardware processor and a hardware memory, the medical data management device 120 may also include a hardware processor and a hardware memory, and the virtual folder management device 130 may also include a hardware processor and a hardware memory, as shown in FIG. 9.

Each of the processors of the control device 110, the medical data management device 120, and the virtual folder management device 130 in some embodiments may be a central processing unit (CPU), a graphics processing unit (GPU), or a dedicated processor in which methods according to some embodiments of the present disclosure are performed. Each of the processors of the control device 110, the medical data management device 120, and the virtual folder management device 130 in some embodiments may have a single core or a plurality of cores. Each of the memories of the control device 110, the medical data management device 120, and the virtual folder management device 130 in some embodiments may be embodied as at least one of volatile storage medium and non-volatile storage medium (i.e., non-transitory storage medium). For example, each of the memories of the control device 110, the medical data management device 120, and the virtual folder management device 130 in some embodiments may include at least one of a read only memory (ROM), and a random-access memory (RAM).

In some embodiments, the control device 110, the medical data management device 120, and the virtual folder management device 130 may be configured as separated server devices. In some other embodiments, the control device 110, the medical data management device 120, and the virtual folder management device 130 may be configured as components of one hardware device corresponding to the integrated medical data management system 10.

In some embodiments, the control device 110 may perform data processing, and may provide results of processing of the medical data to the medical data management device 120 and the virtual folder management device 130.

In some embodiments, the control device 110 may control the overall operation of the integrated medical data management system 10. The hardware processor of the control device 110 may process or execute programs and/or data stored in the hardware memory of the control device 110. For example, the hardware processor of the control device 110 may control various functions of medical integrated medical data management system 10 by executing programs stored in the hardware memory of the control device 110.

In some embodiments, the hardware processor of the control device 110 may perform data processing by using big data and/or machine learning-based data processing scheme.

In some embodiments, the medical data management device 120 may receive and store the original medical data through an input interface of the medical data management device 120. In some embodiments, the input interface may include medical data standard protocols such as DICOM and HL7, file/folder sharing, file/folder export/import, and similar various interfaces.

In some embodiments, the medical data management device receives the medical data from one or more medical imaging equipment such as Computer Tomography (CT) equipment or Magnetic Resonance Imaging (MRI) equipment. For examples, from In some embodiments, medical data to be received at and stored in medical data management services may be high-resolution medical image data, and such high-resolution medical image data may be medical image data obtained by medical imaging equipment such as Computer Tomography (CT) equipment or Magnetic Resonance Imaging (MRI) equipment. For example, the original medical data could be 512×512 or higher resolution CT images, 256×256 or higher resolution MR images, 2000×1500 or higher resolution X-ray images, or 3000× 2500 or higher resolution MG (mammography) images. In addition, pathological data also have super-high-resolution hierarchical pyramid scheme images of over 150,000×100, 000 resolution.

According to some embodiments, the medical data management device 120 may acquire medical data from the Picture Archiving Communication System (PACS). The medical data management device 120 may receive medical data via wireless communication or via wired communication. Such communication can be either local network communication or Internet network communication. Such communication can also be either closed-network communication or open-network communication.

According to an embodiment, the medical data management device 120 may include not only medical image data but also all kinds of data such as text data, voice data, and frame data. The medical data management device 120 may include a large storage device, and may provide the original medical data to the user when the user access information is confirmed by the control device 110.

In some embodiments, the virtual folder management device 130 may generate and store address information indicating medical data stored in the medical data management device 120. According to some embodiments, the virtual folder management device 130 may create a virtual folder according to a user request received from a user device, and store the address information in the generated virtual folder. That is, in some embodiments, the virtual folder management device 130 does not need to store original medical data, and thus, may be configured as a smaller storage device than the medical data management device 120, because the virtual folder management device 130 may store address information having a smaller data size than the original medical data in a virtual folder, and may utilize the stored address information.

The external device 200 is a device distinct from the medical data management device 120, and the external device 200 is not included in the integrated medical data management system 10. The external device 200 may be operated by another operator. The external device 200 may be a separated server device.

In some embodiments, the control device 110 may transmit an access request from the integrated medical data management system 10 to the external device 200, and may provide the user with data included in the external device 200 when access is granted by the external device 200.

The control device 110 of the integrated medical data management system 10 according to some embodiments may generate address information indicating medical data stored in the medical data management device 120 and provide address information to the virtual folder management device 130. In some embodiments, the virtual folder management device 130 may request medical data corresponding to the address information, to the medical data management device 120, through the control device 110, in response to the selection of address information. The control device 110 may identify medical data corresponding to address information, and may provide medical data corresponding to address information, to the user device, through the virtual folder management device 130.

In some embodiments, the medical data management device 120 and the virtual folder management device 130 of the present disclosure may be server devices operated by different operators.

In some other embodiments, the medical data management device 120 and the virtual folder management device 130 of the present disclosure may be server devices operated by the same operator.

In addition, the control device 110 may be composed of hardware elements distinct from the medical data management device 120 and the virtual folder management device 130, which provide processed data to the medical data management device 120 and the virtual folder management device 130.

FIG. 2 is a diagrammatic illustration of an exemplary system for providing medical data to a user according to some embodiments of the present disclosure.

Referring to FIG. 2, a user can access a virtual folder created in the virtual folder management device 130 by accessing the virtual folder management device 130 through the user device 300.

Herein, in some embodiments, the user device 300, the control device 110, the medical data management device 120, and the virtual folder management device 130 may be connected via wireless communication or wired communication. Such connection can be either local network communication or Internet network communication. Such connection can also be either closed-network communication or open-network communication.

In some embodiments, when the user device 300 selects address information stored in the virtual folder, the virtual folder management device 130 may provide the medical data stored in the medical data management device 120 to the user device 300. In some embodiments, in response to receiving from the user device 300, a signal of a selection of address information stored in the virtual folder, the virtual folder management device 130 may automatically transmit the medical data stored in the medical data management device 120 to the user device 300.

According to some embodiments, the user device 300 may transmit first access information and second access information, which are related to the user of the user device 300, to the integrated medical data management system 10. The first access information may be information for a user account to access the virtual folder management device 130, and the second access information may be information for a user account to access the medical data management device 120.

Based on the first access information, the integrated medical data management system 10 may determine whether the user of the user device 300 has a permission to create a virtual folder, and whether the user of the user device 300 has a permission to set a condition for storing medical data in the virtual folder. It may also be determined how many conditions can be set by the user of the user device 300.

In some embodiments, the integrated medical data management system 10 can also set the period of the validity of the first access information. In these embodiments, when the date requested for access from the user account is within the period of the validity of the first access information, the integrated medical data management system 10 allows the user device 300 to access the virtual folder management device 130. By contrast, when the date requested for access from the user account is outside the period of the validity of the first access information, the integrated medical data management system 10 does not allow the user device 300 to access the virtual folder management device 130.

In some embodiments, when the number of conditions that can be set in the virtual folder by the user of the user device 300 is designated as three as the first access information for the user account of the user of the user device 300, the integrated medical data management system 10 can control to set up to three conditions for the virtual folder. The integrated medical data management system 10 may deny the fourth conditions for the virtual folder.

According to some embodiments, the integrated medical data management system 10 may determine whether the user account is a user account with access to the original medical data based on the second access information. For example, the second access information may be a unique management number of the user account, and medical data that may be provided to the user account may be determined according to the authority level of the user account. Accordingly, the integrated medical data management system 10 can maintain the security of the integrated medical data management system 10 by managing medical data that requires high security so that only a small number of users with access can access the original medical data.

Figure 3:
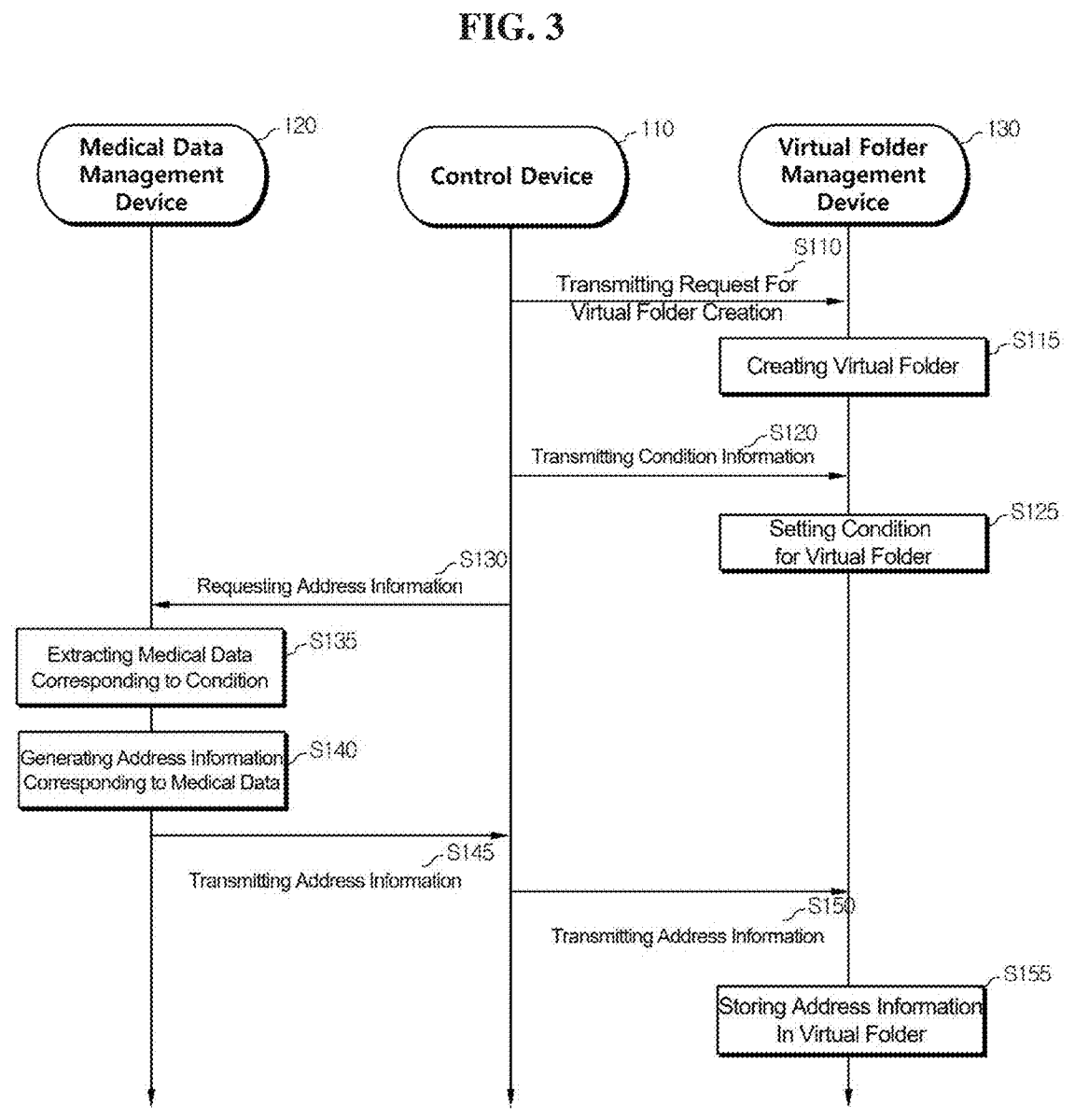

FIG. 3 is a flow chart illustrating an exemplary process of storing address information corresponding to medical data in a virtual folder, according to some embodiments of the present disclosure.

Referring to FIG. 3, the control device 110 may control the virtual folder management device 130 to create a virtual folder in the virtual folder management device 130, and may control the medical data management device to map address information to medical data, and may control the virtual folder management device 130 to store the address information in the virtual folder. In this case, the medical data stored in the medical data management device 120 may be high-security data, and the medical data management device 120 may provide medical data to the control device 110 or the virtual folder management device 130 through an intranet server without being connected to the external device 200. In this way, high security for the original medical data can be maintained. The above operations are further described in the following paragraphs.

In step S110, the control device 110 may transmit a virtual folder creation request to the virtual folder management device 130. According to some embodiments, the control device 110 may obtain a virtual folder creation request and first access information from a user device 300, and may determine whether the virtual folder creation request is a valid request based on the first access information. The control device 110 may transmit the virtual folder creation request to the virtual folder management device 130 in response to a determination that the virtual folder creation request is a valid request.

In step S115, the virtual folder management device 130 may create a virtual folder in the virtual folder management device 130, in response to a receipt of the virtual folder creation request. In this case, the virtual folder may be created correspondingly to a user account of the user of the user device 300, that transmits the first access information to the control device 110. In some embodiments, the created virtual folder may allow access from a user device that transmits the first access information to the control device 110.

In step S120, the control device 110 may transmit information on at least one condition for storing data in the virtual folder, to the virtual folder management device 130. The condition may be set based on the user input from the user device 300. The condition may include one or more specific conditions related to medical data.

In step S125, the virtual folder management device 130 may set at least one condition for storing data in the virtual folder. In this case, the condition may be a condition for storing medical information of medical data in the virtual folder. For example, the condition may be subject information such as the age, gender, diagnosis area, etc. of the subject designated in the medical data, and the type of medical image data may be a specified condition.

In step S130, the control device 110 may request address information corresponding to the medical data, which comply with condition and is stored in the medical data management device 120. The address information may be a unique number referring to medical data, and may be location information in which medical data is stored in the medical data management device 120. Address information is not limited to the above examples, but can be any information that can be distinguished from different medical data and identified by the medical data management device 120.

In step S135, the medical data management device 120 may extract medical data corresponding to the condition transmitted from the control device 110. According to some embodiments, the medical data management device 120 may extract medical information from medical data and determine whether the medical information corresponds to the condition. For example, medical data containing medical image data also contains subject information and medical image types as text information, and text information can be extracted from the medical image data to automatically extract subject information and medical image types. The medical data management device 120 may determine whether the extracted subject information and the type of medical image meet the condition.

According to some other embodiments, tag information may be assigned to each medical data by an input from the user device 300. The user of the user device 300 may be a person who produced medical data. The medical data management device 120 may determine whether the medical data meets the condition by comparing the tag information with the condition.

In step S140, the medical data management device 120 may generate address information corresponding to the extracted medical data. Address information corresponding to the medical data may be mapped to different values for each medical data.

In step S145, the medical data management device 120 may transmit address information to the control device 110.

In step S150, the control device 110 may identify a virtual folder to store address information, and then transmit address information to the virtual folder management device 130.

In step S155, the virtual folder management device 130 may store address information in the virtual folder. In this case, the virtual folder management device 130 stores address information in the virtual folder and can convert address information into user-readable address information so that the user can identify medical data corresponding to the address information.

When a user, through the user device 300, checks the user-readable address information and requests access to medical data mapped to the user-readable address information, the original medical data stored in the medical data management device 120 can be obtained by the user device 300 through the control device 110.

FIG. 4 is a flow chart illustrating an exemplary process of storing external address information from an external device in a virtual folder according to some embodiments of the present disclosure.

Referring to FIG. 4, the control device 110 may store external address information in a virtual folder so that the user device 300 may access data stored in the external device 200 through the integrated medical data management system 10. The external address information may include communication protocol information indicating the external device 200, host address information, and path information. For example, the external address information may be a uniform resource locator (URL) address. In addition, according to some embodiments, the external address information may be information that changes according to address information of medical data, stored in the virtual folder. Embodiments in which the external address information is changed are described later with reference to FIG. 7.

In step S210, the control device 110 may transmit a virtual folder creation request to the virtual folder management device 130. In step S215, the virtual folder management device 130 may create a virtual folder, in response to the virtual folder creation request. Since this process of creating the virtual folder are similar to the process described above with reference to FIG. 3, detailed descriptions thereof are omitted here.

In step S220, the control device 110 may request external address information indicating data stored in the external device 200. In some embodiments, the external address information has lower security characteristics than the address information corresponding to the original medical data stored in the medical data management device 120. For example, more complex encryption is performed on information on the address information corresponding to the original medical data stored in the medical data management device 120, than that of the external address information.

In some embodiments, the external device 200 may require a lower security level than the medical data management device 120 of the integrated medical data management system 10, and the control device 110 may access data stored in the external device 200 without access authority to data stored in the medical data management device 120. For example, the external address information may be URL information, but is not limited thereto, and may be link information that may access an external intranet device.

In step S225, the external device 200 generates external address information corresponding to the external address information request. In step S230, the external device 200 may transmit external address information to the control device 110.

In step S235, the control device 110 may transmit external address information to the virtual folder management device 130. In step S240, the virtual folder management device 130 may store external address information in the virtual folder.

Figure 5:
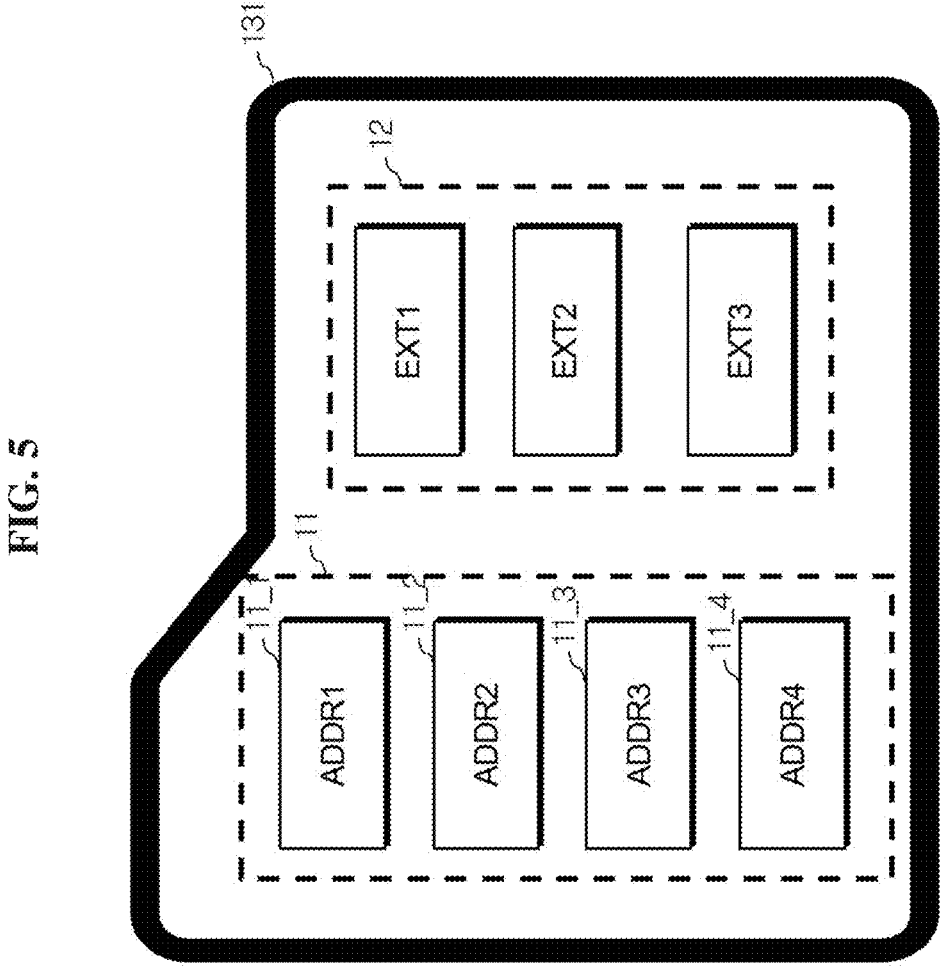
FIG. 5 is a diagrammatic illustration of an exemplary virtual folder in which address information and external address information are stored, according to some embodiments of the present disclosure.

FIG. 5 is a diagrammatic illustration of an exemplary virtual folder in which address information and external address information are stored, according to some embodiments of the present disclosure.

Referring to FIG. 5, the virtual folder 131 may store address information 11 corresponding to medical data stored in the medical data management device 120, and external address information 12 corresponding to external data stored in the external device 200. In some embodiments, the external address information 12 may be configured independently and separately from the address information 11. In some other embodiments, the external address information 12 may be configured to have different values corresponding to the address information 11. In some embodiments, the external address information 12 is stored in a first virtual folder, and the address information 11 is stored in a second virtual folder, which is separately configured from the first virtual folder. In some embodiments, the diagrammatic illustration shown in FIG. 5 is displayed on a user device 300 as an image icon, to deliver visual image information regarding how folders are configured in the virtual folder management device 130.

In some embodiments, when the external address information 12 is configured independently from the address information 11, the external address information 12 may be referred to as static address information. When the external address information 12 is configured to be dependent on the address information 11, the external address information 12 may be referred to as dynamic address information. The embodiments related to the static address information are described in FIG. 6, and the embodiments related to the dynamic address information are described in FIG. 7.

FIG. 6 is exemplary medical data provided to a user based on static address information according to some embodiments of the present disclosure.

Referring to FIG. 6, data stored in the external device 200 corresponding to the static address information 12a may be text data. For example, the static address information 12a may be a URL address, and the URL address may include communication protocol information, host information, and route information. The external device 200 may be a host server corresponding to host information of a URL address.

For example, in the static address information 12a, "https" may be communication protocol information, "blog.xxx.com" may be host information, and "medical journalist/aaa" may be path information. That is, the integrated medical data management system 10 may load text data from a host server device indicated by "blog.xxx.com" through a path indicated by "medical journalist/aaa". In this case, the loaded information may be temporarily stored in the integrated medical data management system 10 and then provided to the user.

Figure 7:
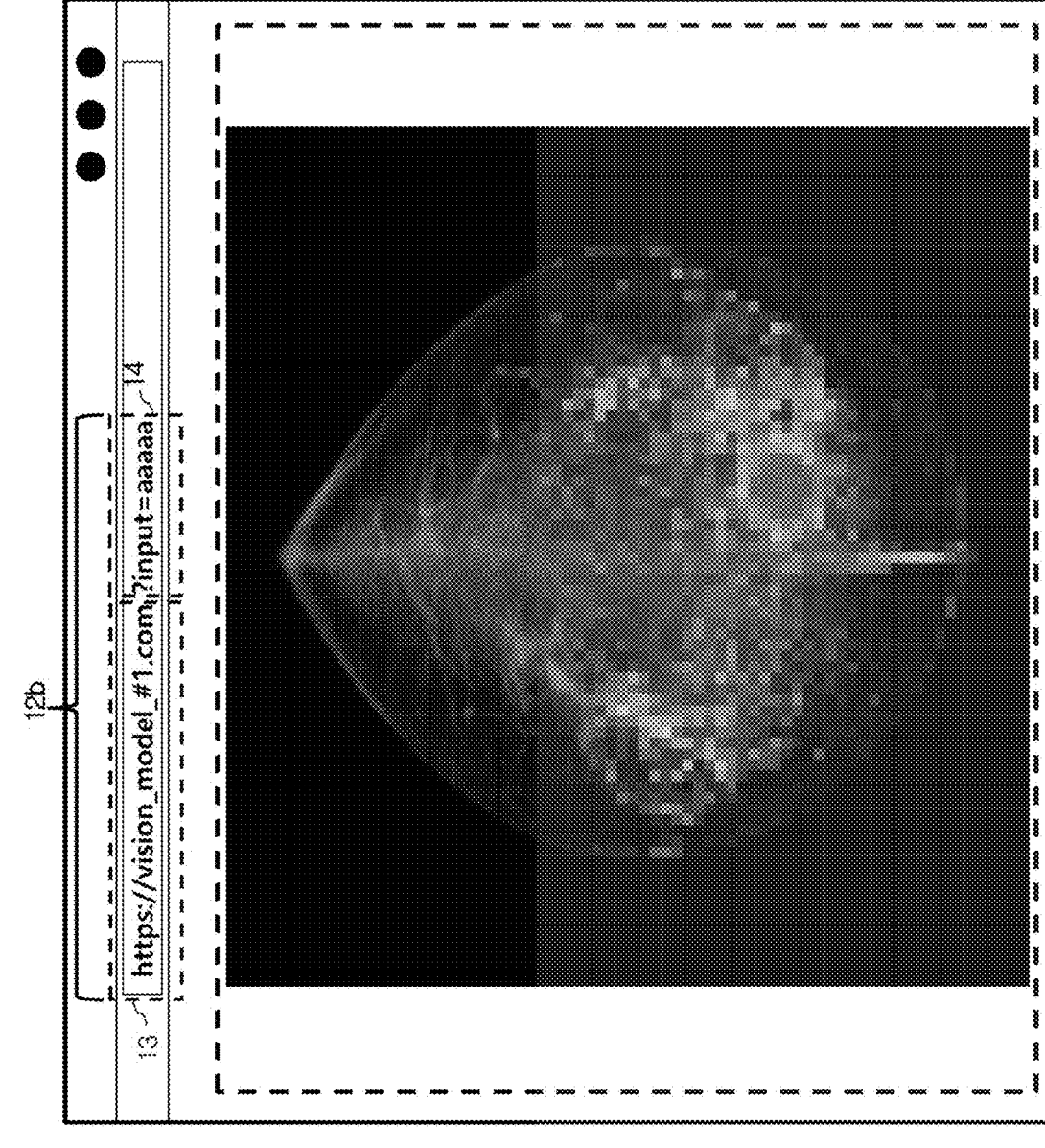
FIG. 7 is exemplary medical data provided to a user based on dynamic address information according to some embodiments of the present disclosure.

FIG. 7 is exemplary medical data provided to a user based on dynamic address information according to some embodiments of the present disclosure.

Referring to FIG. 7, the integrated medical data management system 10 may generate dynamic address information 12b based on address information stored in a virtual folder. According to some embodiments, medical data to generate dynamic address information 12b may be selected by the user through a user input to the user device 300, and the integrated medical data management system 10 may generate dynamic address information 12b based on address information corresponding to the selected medical data.

Referring to FIG. 5, when the first address information 11_1 is selected by the user, the integrated medical data management system 10 may generate first dynamic address information corresponding to the first address information 11_1, and when the second address information 11_2 is selected by the user, the integrated medical data management system 10 may generate second address information 11_2. In this case, the first dynamic address information and the second dynamic address information may be different information.

Referring to FIG. 7, the integrated medical data management system 10 may generate dynamic address information 12b by adding address information 14 to external address information 13 stored in a virtual folder. In this case, the external address information 13 may be a URL address, and may consist of only communication protocol information and host information. Unlike static address information including route information at a fixed value, the integrated medical data management system 10 can generate dynamic address information 12b by adding path information generated based on address information 14 to protocol information and host information of the external address information 13.

For example, the integrated medical data management system 10 may store, in a virtual folder, external address information 13 having "https://vision_model_#1.com" as protocol information and host information. In this case, when the user requests medical data corresponding to address information 14 that is "aaaa", the integrated medical data management system 10 may generate dynamic address information 12b by adding path information that is "input=aaaaa" to "https://vision_model_#1.com". Accordingly, the integrated medical data management system 10 may generate "https://vision_model_#1.com?input=aaaaa", in which address information 14 that is "aaaaa" is added to the query parameter, as dynamic address information 12b. Alternatively, the integrated medical data management system 10 may generate "https://vision_model_#1.com/input/aaaaa" in which address information 14 that is "aaaaa", is added to the path information, as dynamic address information 12b.

That is, the integrated medical data management system 10 may generate dynamic address information based on address information of medical data requesting data processing and information of the external device 200 storing function data performing data processing. In some embodiments, the integrated medical data management system 10 may store, in a virtual folder, only address information indicating a location in the medical data management device 120, storing medical data, and external address information indicating a location in the external device 200, storing function data. In these embodiments, the integrated medical data management system 10 may efficiently analyze medical data using less storage space. In addition, the integrated medical data management system 10 may allow the user to select only medical data to perform data processing and function data to perform data processing, thereby increasing user convenience.

The method of generating dynamic address information by the integrated medical data management system 10 is not limited to adding address information corresponding to medical data to the URL address, but also includes embodiments in which different dynamic address information is generated according to address information for a location in which function data is stored and address information for a location in which medical data is stored.

For example, the integrated medical data management system 10 may set an Application Programming Interface (API) address of the system implemented by the Representational State Transfer (REST) architecture as external address information. A system implemented as the REST architecture may also be referred to as RESTful. The API address may be an address for calling function data stored in an external device.

The API address may include resource information, operation information, and expression information. The resource information may be information on a resource connected to a system implemented by a REST architecture, and may be identification (ID) information for distinguishing a resource in which function data is stored. The ID information may be configured as an HTTP Uniform Resource Identifier (URI), for example.

The operation information may be information requested to be performed on a resource corresponding to the resource information, and for example, may include CRUD data. The types of CURD data may include Create request data, Read request data, Update request data, and Delete request data.

The expression information is information on the format in which the integrated medical data management system and the external device exchange data, and may include JSON, XML, RSS, and TEXT formats, for example.

According to some embodiments, the integrated medical data management system 10 may access function data of an external device based on an API address comprising resource information, operation information, and expression information, and may perform operations on function data according to operation information. For example, in the case of operation information comprising CRUD data, when the type of CRUD data is Create request data, the data to be created can be created on an external device or resource. When the type of CRUD data is Read request data, the integrated medical data management system can load function data from the external device or resource. When the type of CRUD data is Update request data, data existing in an external device or resource may be updated. When the type of CRUD data is Delete request data, data existing in an external device or resource may be deleted.

According to some other embodiments, the integrated medical data management system can call an executable file stored on an external device as function data, and perform operations on medical data by specifying medical data to be input into the function data. An executable file may be, for example, software, and an external device may consist of a Software as a Service (SaaS) network that allows a user to take and use computing software as much as they need. In this case, the external address information may be information indicating software capable of performing computational processing on medical data among SaaS networks, and the software capable of performing computational processing may be function data.

FIG. 8 is a flow chart illustrating an exemplary process of providing result data for medical data after confirming user access information, according to some embodiments of the present disclosure.

Referring to FIG. 8, when the user device 300 transmits a request signal to the integrated medical data management system 10 for analysis data, the control device 110 may provide the analysis data to the user device 300 based on address information and external address information stored in the virtual folder management device 130.

In step S310, the control device 110 may receive an analysis data request from the user device 300. In this case, the control device 110 may receive access information on the user account of the user device 300, information on medical data for analysis, and a type of function data. For example, the function data may be a neural network model, or an analysis model built in the external device 200.

In step S315, the control device 110 may check the access information of the user account to determine whether the user is permitted for the analysis. For example, the control device 110 may determine whether the user account is allowed to access the virtual folder and the medical data management device 120, and may determine whether the user account is allowed to use the function data stored in the external device 200. In some embodiments, step S315 is automatically performed by the control device 110, in response to a receipt of the analysis data request from the user device 300.

When the user access information is confirmed, in step S320, the control device 110 may transmit the address information received from the user device to the virtual folder management device 130. In step S325, the virtual folder management device 130 may request medical data corresponding to the received address information, to the medical data management device 120. In step S330, the medical data management device 120 may transmit medical data corresponding to address information to the control device 110.

In step S335, the control device 110 may analyze the received medical data. In this case, the function data for the control device 110 to perform the analysis may be data corresponding to the type of function data requested by the user, and the control device 110 may load the function data from the external device 200.

However, the embodiments are not limited to the control device 110 directly receiving function data and medical data, but may also include providing medical data to the external device 200 and receiving the result data processed by the external device 200. That is, the embodiments are not limited to the control device 110 performing data processing directly, but may also include the control device 110 performing only intermediation for data processing.

In some embodiments, the external device may be a server device providing data analysis based on artificial intelligence (AI) technology. In some embodiments, results of bone age (score method), progression rate of degenerative brain disease, and lung disease findings information could be the analysis data.

In step S340, the control device 110 may transmit data-processed analysis data to the user device 300. The data-processed analysis data may be images, figures, waveforms, graphs, and et al.

After receiving data, the user device 300 may perform various types of operations. For example, the user device 300 may automatically perform grouping of received data according to pre-set classification criteria. The received data may also be grouped, de-identified, or extracted by research data search conditions (cohort generation conditions), or used as artificial intelligence (AI) learning data to be compared to the original data. In some embodiments, the received data may also be inputted into AI learning model by using a neural network.

In some embodiments, after receiving data from to the integrated medical data management system 10, the user device 300 may display an image based on the received data, as exemplary shown in FIGS. 6 and 7. In some embodiments, the user device 300 may also receive one or more user inputs to navigate or manipulate the image displayed on the user device 300.

Exemplary embodiments have been disclosed in the drawings and specifications as described above. Embodiments have been described using specific terms in the present specification, but this is used only for the purpose of describing the technical idea of the present disclosure and is not used to limit the scope of the present disclosure described in the meaning or patent claims. Therefore, those of ordinary skill in the art will understand that various modifications and equal other embodiments are possible from this. Therefore, the true technical scope of protection of the present disclosure should be determined by the technical idea of the appended claims.

The effects of the present disclosure are not limited to the effects mentioned above. Other effects not mentioned will be clearly understood by those skilled in the art from the above description.

While the present disclosure has been described with reference to exemplary embodiments, it will be apparent to those skilled in the art that various changes and modifications may be made without departing from the spirit and scope of the inventive concept. Therefore, it should be understood that the above embodiments are not limiting, but illustrative.

While the present disclosure has been shown and described with reference to particular embodiments thereof, it will be understood that the present disclosure can be practiced, without modification, in other environments. The foregoing description has been presented for purposes of illustration. It is not exhaustive and is not limited to the precise forms or embodiments disclosed. Modifications and adaptations will be apparent to those skilled in the art from consideration of the specification and practice of the disclosed embodiments. Additionally, although aspects of the disclosed embodiments are described as being stored in memory, one skilled in the art will appreciate that these aspects can also be stored on other types of computer readable media, such as secondary storage devices, for example, hard disks or CD ROM, or other forms of RAM or ROM, USB media, DVD, Blu-ray, or other optical drive media.

Computer programs based on the written description and disclosed methods are within the skill of an experienced developer. Various programs or program modules can be created using any of the techniques known to one skilled in the art or can be designed in connection with existing software. For example, program sections or program modules can be designed in or by means of .Net Framework, .Net Compact Framework (and related languages, such as Visual Basic, C, etc.), Java, C++, Objective-C, HTML, HTML/AJAX combinations, XML, or HTML with included Java applets.

Moreover, while illustrative embodiments have been described herein, the scope of any and all embodiments having equivalent elements, modifications, omissions, combinations (e.g., of aspects across various embodiments), adaptations and/or alterations as would be appreciated by those skilled in the art based on the present disclosure. The limitations in the claims are to be interpreted broadly based on the language employed in the claims and not limited to examples described in the present specification or during the prosecution of the application. The examples are to be construed as non-exclusive. Furthermore, the steps of the disclosed methods may be modified in any manner, including by reordering steps and/or inserting or deleting steps. It is intended, therefore, that the specification and examples be considered as illustrative only, with a true scope and spirit being indicated by the following claims and their full scope of equivalents.

What is claimed is:

1. An integrated medical management system comprising:
a medical data management device comprising a hardware processor and a hardware memory;
a virtual folder management device comprising a hardware processor and a hardware memory;
a control device comprising a hardware processor and a hardware memory; and
a user device,
wherein the hardware processor of the medical data management device is configured to:
receive medical data through an input interface of the medical data management device;
store the received medical data in the hardware memory of the medical data management device; and
transmit the stored medical data to at least one selected from the group consisting of the virtual folder management device, the control device, and one or more external devices,
wherein the hardware processor of the virtual folder management device is configured to:
create a virtual folder in the hardware memory of the virtual folder management device; and
store, in response to a request for storing, received from the user device, address information corresponding to a particular part of the stored medical data, in the virtual folder,
wherein the hardware processor of the control device is configured to:
set at least one condition related to the virtual folder; and
control the medical data management device and the virtual folder management device to selectively store the address information that meets the at least one condition, in the virtual folder,
wherein the hardware processor of the virtual folder management device is configured to:
transmit, in response to a request for accessing, received from the user device, the particular part of the stored medical data, corresponding to the address information, to the user device,
wherein the user device configured to:
automatically perform grouping of received data according to pre-set classification criteria;
display an image based on the particular part of the stored medical data, and provide medical information in response to a user input entered into the user device; and
forward the particular part of the stored medical data to a neural network for performing machine learning by using the particular part of the stored medical data, and
wherein the address information comprises:
first address information indicating a location of first medical data stored in the medical data management device, wherein the first address information is configured to be stored in a first virtual folder; and
second address information indicating a location of second medical data stored in an external device, which is separately configured from the medical data management device, wherein the second address information is configured to be stored in a second virtual folder, which is separately configured from the first virtual folder, and the second medical data has a lower security level than a security level of the first medical data.

2. The integrated medical management system according to claim 1, wherein the hardware processor of the control device is further configured to:

identify tag information inputted by a user device for the medical data;

determine whether the identified tag information meets the at least one condition; and when the identified tag information meets the at least one condition, store the address information corresponding to the medical data corresponding to the tag information, in the virtual folder.

3. The integrated medical management system according to claim 1, wherein the second address information is static address information, which is not changed even though the second medical data is changed.

4. The integrated medical management system according to claim 1, wherein the second address information is dynamic address information, which is changed as the second medical data is changed.

5. The integrated medical management system according to claim 4, wherein the hardware processor of the control device is further configured to:

when the dynamic address information is loaded on the control device according to an input from the user device, transmit the medical data corresponding to the dynamic address information, selected from the stored medical data in the medical data management device, to the external device.

6. The integrated medical management system according to claim 4, wherein the hardware processor of the control device is further configured to:

when the dynamic address information is loaded on the control device according to the input from the user device, load a function corresponding to the dynamic address information from the external device, and perform data processing on the medical data corresponding to the dynamic address information, selected from the stored medical data in the medical data management device, and transmit the medical data corresponding to the dynamic address information, selected from the stored medical data in the medical data management device, to the external device.

7. The integrated medical management system according to claim 4, wherein the dynamic address information is stored in the external device and includes a function for performing data processing on the medical data, and wherein the hardware processor of the control device is further configured to:

when the dynamic address information is loaded on the control device according to the input from the user device, perform data processing on the medical data corresponding to the dynamic address information, selected from the stored medical data in the medical data management device, and transmit a result data of the data processing to the user device.

8. The integrated medical management system according to claim 4, wherein the hardware processor of the control device is further configured to:

acquire function data stored in an external device based on an application programmatic interface (API) address comprising resource information, operation information, and expression information; and perform data processing on the medical data corresponding to address information specified by the user device, based on the function data.

9. The integrated medical management system according to claim 4, wherein the hardware processor of the control device is further configured to:

acquire, as function data, an executable file stored in the external device; and perform data processing on the medical data corresponding to address information specified by the user device, based on the function data.

10. The integrated medical management system according to claim 3, wherein the static address information includes communication protocol information, host information, and path information.

11. The integrated medical management system according to claim 4, wherein the dynamic address information includes path information generated based on address information corresponding to the medical data, and protocol information and host information of the external address information.

12. The integrated medical management system according to claim 1, wherein the medical data management device is configured to receive the medical data from one or more medical image capturing devices comprising one or more cameras.

* * * * *